US006369280B1

(12) United States Patent
Tamminen et al.

(10) Patent No.: US 6,369,280 B1
(45) Date of Patent: Apr. 9, 2002

(54) PROCESS FOR PREPARING ALKYL ETHERS AND MIXTURES THEREOF

(75) Inventors: Esa Tamminen, Espoo; Petri Lindqvist, Porvoo, both of (FI)

(73) Assignee: Neste Oy, Espoo (FI)

( * ) Notice: Subject to any disclaimer, the term of this patent is extended or adjusted under 35 U.S.C. 154(b) by 0 days.

(21) Appl. No.: 09/640,893

(22) Filed: Aug. 17, 2000

Related U.S. Application Data

(63) Continuation-in-part of application No. 09/091,572, filed as application No. PCT/FI96/00678 on Dec. 19, 1996, now abandoned.

(30) Foreign Application Priority Data

Dec. 22, 1995 (FI) .................................................. 956256

(51) Int. Cl.$^7$ .............................................. C07C 41/00
(52) U.S. Cl. ..................................................... 568/697
(58) Field of Search .......................................... 568/697

(56) References Cited

U.S. PATENT DOCUMENTS

| 3,940,450 A | * | 2/1976 | Lee ............................. 260/614 |
| 4,198,530 A | | 4/1980 | Wentzheimer et al. |
| 4,440,963 A | * | 4/1984 | Childs ......................... 568/697 |
| 4,475,005 A | | 10/1984 | Paret |
| 4,503,265 A | | 3/1985 | Schleppinghoff et al. |
| 4,647,703 A | | 3/1987 | Torck et al. |
| 4,820,877 A | * | 4/1989 | Harandi ....................... 568/697 |
| 5,106,389 A | * | 4/1992 | Hsrandi ........................ 44/449 |
| 5,118,873 A | * | 6/1992 | Smith .......................... 568/697 |
| 5,536,886 A | | 7/1996 | Tamminen et al. |
| 5,536,887 A | * | 7/1996 | Minkkinen ................... 568/697 |
| 5,600,024 A | * | 2/1997 | Eldridge ...................... 568/697 |
| 5,637,777 A | | 6/1997 | Aittama et al. |
| 5,679,872 A | * | 10/1997 | Streicher .................... 568/699 |
| 5,852,220 A | * | 12/1998 | Jarvelin ...................... 568/697 |
| 5,919,989 A | * | 7/1999 | Bakshi ........................ 568/698 |

FOREIGN PATENT DOCUMENTS

| EP | 0078422 | 7/1985 |
| EP | 0323134 | 7/1989 |
| EP | 0 323 134 A1 | 7/1989 |
| EP | 0469285 | 2/1992 |
| EP | 0 469 285 A1 | 2/1992 |
| EP | 0502265 | 9/1992 |
| EP | 0 502 265 A2 | 9/1992 |
| GB | 1594158 | 2/1978 |

* cited by examiner

Primary Examiner—Michael L. Shippen
(74) Attorney, Agent, or Firm—Birch Stewart Kolasch & Birch, LLP.

(57) ABSTRACT

The invention relates to a process for preparing tertiary alkyl ethers, in particular MTBE, ETBE or mixtures of these ethers with heavier ethers. According to the process the feedstock containing hydrocarbons is fed to a catalytic distillation reactor system, in which the isoolefines, in particular the $C_4$ to $C_7$ isoolefines, of the feed are reacted with an alkanol in the presence of a cation exchange resin in order to produce tertiary alkyl ether products. The reaction product containing the ethers is removed from the distillation system as the bottoms product and, if necessary, it is subjected to an additional treatment for producing a gasoline component. The unreacted alkanol is removed as the overhead product of the distillation. According to the invention, the distillate withdrawn mainly contains an azeotrope of $C_3$ hydrocarbons and alkanol, the $C_3$ amount of which at least approximately corresponds to the $C_3$ hydrocarbon concentration of the hydrocarbon feed, a substantial amount of the unreacted alkanol being removed in the form of said azeotrope. By means of the invention the need for a separate alkanol washing unit is eliminated in the apparatus which considerably reduces apparatus investment costs.

13 Claims, 2 Drawing Sheets

PROCESS FOR PREPARING ALKYL ETHERS AND MIXTURES THEREOF

This application is a continuation-in-part of co-pending application Ser. No. 09/091,572, filed on Jul. 22, 1998. Application No. 09/091,572 is the national phase of PCT International Application No. PCT/FI96/00678 filed on Dec. 19, 1996 under 35 U.S.C. §371. The entire contents of each of the above-identified applications are hereby incorporated by reference.

BACKGROUND OF THE INVENTION

1. Field of the Invention

The present invention concerns a process for preparing tertiary alkyl ether products which are used, in particular, as a components of motor fuels. The products contain, for instance methyl t-butyl ether, ethyl t-butyl ether, t-amyl methyl or t-amyl ethyl ethers and possibly heavier tertiary alkyl ethers. According to the process, the isoolefins, in particular the $C_4$–$C_7$ isoolefins of the feedstock are reacted with a suitable alkanol for preparing the corresponding ethers. These ethers are removed together with the bottoms product of the distillation-reaction system and, if necessary, they are further processed in order to prepare a motor fuel component. Unreacted alkanol is removed with the overhead product of the distillation.

2. Description of Related Art

In order to improve the anti-knocking characteristics of motor fuels without using organolead compounds, and in order to reduce the concentration of detrimental components in the exhaust gases, tertiary alkyl ethers are added to the fuels. The oxygen-containing ether group of these compounds has been found to improve the combustion process in a favorable way as far as the aforementioned aspects are concerned. Suitable alkyl tert-alkyl ethers are methyl t-butyl ether (MTBE), ethyl t-butyl ether (ETBE), t-amyl methyl ether (TAME), t-amyl ethyl ether (TAEE) and t-hexyl methyl ether (THME), just to mention a few examples. These ethers are prepared by etherification of a monovalent aliphatic alcohol with an isoolefin. These olefins include, but are not limited to isobutene, 2-methyl-1-butene (2M1B), 2-methyl-2-butene (2M2B), 2-methyl-1-pentene (2M1P), 2-methyl-2-pentene (2M2P) and 2,3-dimethyl-1-pentene (23DMP). The reaction can be carried out in a fixed bed reactor, in a fluidized bed reactor, in a tubular reactor or in a catalytic distillation column.

In a fixed bed reactor, the feed components are reacted in the presence of a solid catalyst particles, said catalyst particles being contained in a layer which remains unmixed, because the liquid flow rates are so low that the catalyst particles do not separate from each other. They form a so-called fixed bed. On the other hand, in a fluidized bed reactor, the flow rate of the liquid phase is so high that the catalyst particles float separately in the fluidized bed of the reactor.

When the etherification is carried out in a catalytic i.e. reactive distillation process, the catalyst particles can form a fixed or fluidized bed in the column. The particular benefit which can be obtained by the catalytic distillation process is that the reaction and the separation of the products take place in the same vessel.

The etherification reaction is an exothermic equilibrium reaction, and the maximum conversion is determined by the thermodynamic equilibrium of the reaction system. Typically, by carrying out reaction and separation in one and the same reactive distillation column, it is possible to obtain an about 99% conversion in the case of MTBE, whereas only a 95% conversion is obtainable in a fixed bed reactor. The improvement in conversion for heavier ethers is even more significant. In case of TAME the conversion increases from 65% to 90%.

Ion exchange resins can be used as catalysts. Generally the resin used comprises a sulfonated polystyrene/divinyl benzene based cation exchange resin (sulfonated polystyrene cross-linked with divinyl benzene) having particle sizes in the range from 0.1 to 1 mm.

In case of MTBE (or ETBE) there are mainly two types of processes available. Both types have been in commercial use for more than 15 years. In the first commercial process for MTBE fixed bed reactors are used. The reaction section is followed by distillation in order to separate unreacted components from formed ether. One of the unreacted components is methanol, which is then separated by means of a water wash and a distillation. This recovered methanol is normally recycled back to the reactor feed. This kind of process is explained in more detail in the patent U.S. Pat. No. 4,198,530.

In order to improve the economics of the process, part of the catalyst was placed into the product distillation column. The principle is called reactive distillation and it lead to increased ether conversion, because the reaction and the separation of feeds and products is performed simultaneously.

The simultaneous removal of reaction product drives the process beyond the chemical equilibrium barrier. This process has been described in a number of patents. Placing the catalyst within a distillation column has, unfortunately, also drawbacks, which originate from feed impurities, which are poisons to the ion-exchange catalyst used. In some cases, depending on the feed origin, these impurities have to be removed before the etherification process. Otherwise the catalyst activity is gradually lost making the unit performance uneconomical due to lower conversion levels. If the catalyst within the distillation column needs to be replaced, it always means that the whole unit has to be shut down. Another drawback is that the catalyst used inside column is much more expensive the one used in fixed bed reactors.

Some processes try to avoid this costly catalyst placement by using a fixed bed reactor, which is coupled to the distillation column as a side reactor. One example is described in the U.S. Pat. No. 4,503,265. For some reason, however, there has been hardly any commercial success with this kind of processes in the MTBE production.

The use of reactive distillation does not, however, eliminate the need for separation and recycling of the alcohol used as a second feedstock. These operations increase the required investment costs and also burden the economics by creating additional operating costs. Also, because of the alcohol recycle, any feed impurities which travel along with alcohol build up within the unit generating even more stringent feed pretreatment requirements.

There are three alternative TAME preparation processes available. Two of these are older and use the same principles as described above for MTBE-production.

The third and newest process for preparation of TAME and also of heavier ethers is described in our international patent applications WO 93/19031 and WO 93/19032. It uses the side reactor principle in order to avoid the costly catalyst placement inside a distillation column. The main difference between to that process and the two others is, however, that it does not need alcohol separation and recycle. This is possible by unique utilization of alcohol-hydrocarbon azeotropes within the distillation column. The process can also use $C_5$–$C_7$ hydrocarbons as a feedstock. Said process is in commercial use.

So far almost all commercial etherification units produce only one ether as main product with the exception of above described third TAME process. Simultaneous production of ethers from $C_4$–$C_7$ hydrocarbons leads to some problems for example regarding catalyst placement. If a reactive distillation process is used the reactants build up in different sections of the distillation column requiring a wider placement of catalyst and making the internal flows and increasing the size of the columns. Furthermore, the simultaneous production of MTBE and THME is not possible with reactive distillation, since MTBE and the $C_6$ hydrocarbons, which form THME, have boiling points that lie within the same range.

If prior art processes are used for simultaneous mixed ether production (MTBE/TAME/THME), alcohol separation and recycle is required. Even the third TAME process requires an alcohol processing section, since the $C_4$–$C_7$ hydrocarbon feedstock contains too much $C_4$ hydrocarbons which do not react and thus make the distillate flow significantly larger than with a $C_5$–$C_7$ hydrocarbon feedstock. Since alcohol leaves the distillation column in the form of an azeotrope, the amount of alcohol in the distillate of mixed ether processes is unacceptable for downstream processes like alkylation, thus requiring the alcohol to be separated from the distillate.

Similar problems are encountered with all alkanols.

SUMMARY OF THE INVENTION

The present invention aims at eliminating the problems associated with the prior art by providing a completely novel process for producing tertiary alkyl ethers.

The invention is based on the concept of operating the product distillation of a catalytic distillation reactor system in such a way that most, and preferably practically all, of the alkanol which is removed with the distillate is bound to hydrocarbons, which are lighter than any of the reactive or unreactive $C_4$–$C_7$ hydrocarbons present in the feedstock.

It is known per se that, e.g., methanol forms an azeotrope with the components present in etherification mixtures of tertiary alkyl ethers. There are several applications known, wherein the unreacted methanol is removed from the top of the distillation column together with $C_4$ hydrocarbons. Prior art processes of this kind are described in, e.g., the Published German Patent Application No. 2,705,538, the Published European Patent Application No. 78,422, U.S. Pat. No. 4,198,530 and the Swedish Applications Laid Open Nos. 448,452 and 459,175.

According to the present invention, the hydrocarbons lighter than any of the reactive or unreactive $C_4$–$C_7$ hydrocarbons possibly present in the feedstock are mainly removed with the overhead product (distillate) of the distillation. Therefore, the overhead product withdrawn from distillation substantially contains an azeotrope formed by the $C_3$ hydrocarbons and the alkanol used. The amount of $C_3$ hydrocarbons in the distillate corresponds at least approximately to the amount of $C_3$ hydrocarbons present in the feed. In this way, an essential part of the unreacted alkanol is removed in the form of said azeotrope. The bottoms product of the distillation contains virtually all inert or unreacted $C_4$–$C_7$ hydrocarbons present in the feedstock along with formed ethers.

In particular, the process according to the present invention is characterized by the following steps:

feeding a feedstock containing hydrocarbons, in particular $C_{3-7}$, hydrocarbons, to a catalytic distillation reactor system, reacting the $C_{4-7}$ isoolefines of the feedstock with an alkanol in the presence of a catalyst to form tertiary alkyl ethers, removing the alkyl ethers from the distillation reactor and substantially all of the unreacted and inert hydrocarbons with the bottoms product of the distillation, and withdrawing an overhead product, which mainly contains an azeotrope of $C_3$ hydrocarbons and the alkanol.

The $C_3$ amount of the withdrawn overhead product corresponds essentially to the amount of $C_3$ hydrocarbons in the feedstock, whereby an essential part of the unreacted alkanol is removed in the form of said azeotrope.

The ether product preferably comprises MTBE or ETBE and the hydrocarbon feed contains primarily reactive $C_4$ hydrocarbons.

DETAILED DESCRIPTION OF THE INVENTION

Figure 1:
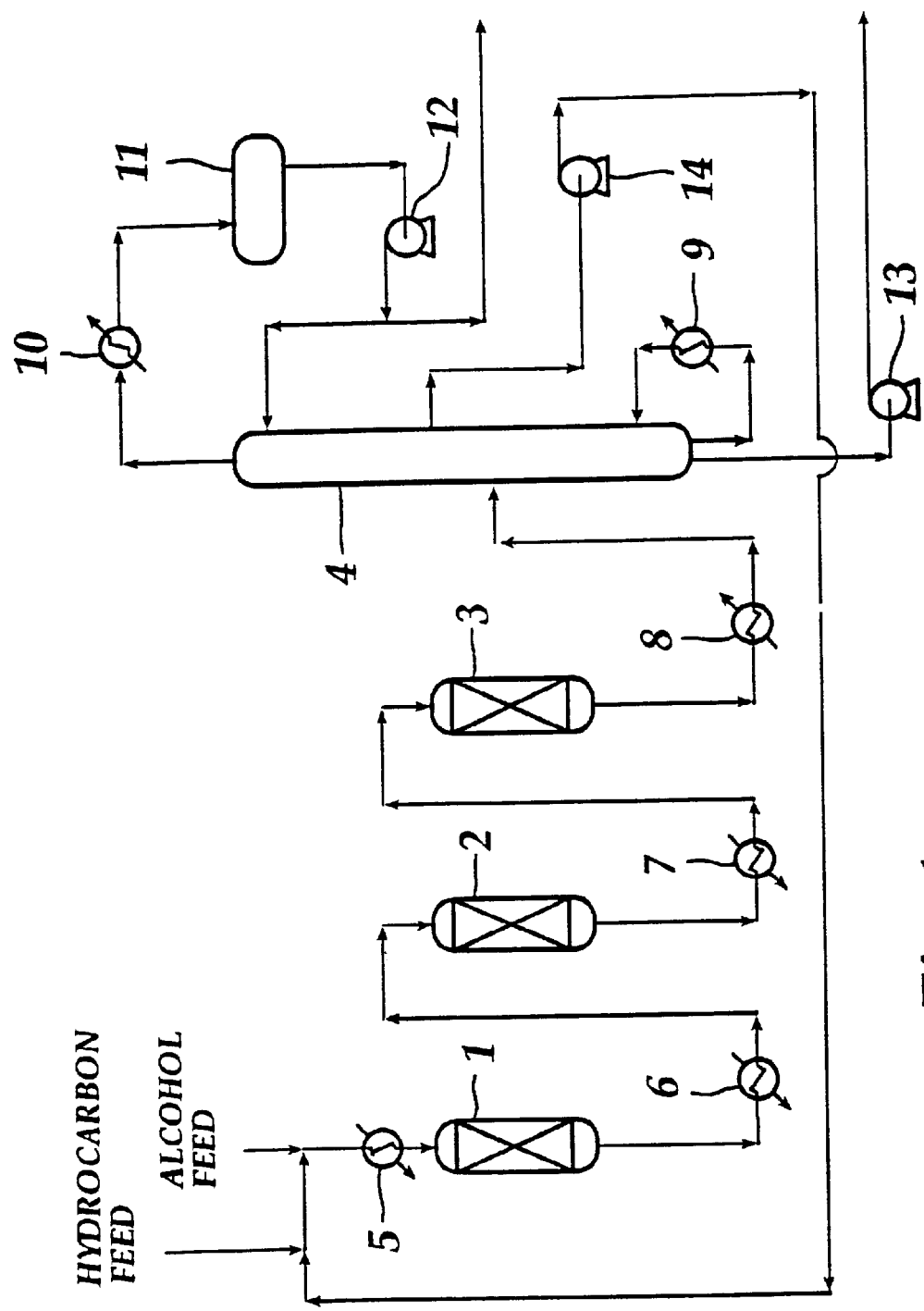
FIG. 1 depicts a simplified scheme of an etherification process according to the invention.

The production of the ether may be carried out in a "catalytic distillation reactor system", wherein the ether product reaction and the separation of the products take place at least partially simultaneously. Such an apparatus typically comprises a conventional reactive distillation column or a distillation column combined with at least one side reactor. Reference is made to the embodiments described in greater detail in International Patent Applications WO 93/19031 and WO 93/19032.

However, the present invention can also be carried out in a conventional etherification system comprising a number of reactors in a cascade connected to at least one distillation column designated for product separation.

Typically, in the latter process configuration also depicted in the attached drawings, the feed hydrocarbons together with the alcohol (methanol and/or ethanol) and the recycle stream from the fractionator are fed to the first etherification reactor after cooling to the specific reaction temperature. The effluent from the first reactor is cooled and fed to a second etherification reactor. The effluent from the second reactor is cooled and fed to third etherification reactor. The effluent is then heated and fed to the main fractionator, which is operated according to the principles laid down in WO 93/19032, i.e. so that the distillate consist of mainly $C_3$ hydrocarbons and the alcohol, which is in azeotropic concentration in the distillate. The amount of unreactive feed $C_3$'s therefore fixes the amount of distillate. A side draw-off is taken out above feed point and fed to the first reactor via heater. The bottom product consists of unreacted hydrocarbons and the ethers formed.

In comparison, according to the side reactor configuration, the hydrocarbons and the alkanol are fed into the side drawoff, which is conducted to at least one side reactor, connected to the distillation column. Having passed the side reactor(s) the reaction mixture is returned to the distillation column, preferably at a point below the feed point.

The term "alkanol" includes lower alkyl alcohols capable of forming azeotropes with the saturated and unsaturated hydrocarbons, in particular the $C_3 \ldots C_7$-hydrocarbons, of the hydrocarbon feedstock. As specific examples of the alkanols; the following can be mentioned: methanol, ethanol, n-propanol, i-propanol, n-butanol, i-butanol and t-butanol, methanol and ethanol being particularly preferred.

The term "olefinic hydrocarbon feedstock" or "hydrocarbon feedstock" (which are interchangeably used herein), is intended to cover all hydrocarbon feedstocks, which contain a mixture of isoolefins which can be etherified to form tertiary alkyl ethers. In particular, the following feedstocks are preferred: $C_4$ fractions from FCC, TFF or RCC, FCC Gasoline, FCC Light Gasoline, Pyrolysis $C_5$ Gasoline, TCC Gasoline, RCC and Coker Gasoline. The feed can also comprise a mixture of two or more olefinic hydrocarbon feedstocks, such as a mixture of FCC Light Gasoline and a pyrolysis $C_5$ cut. The proportion of the various $C_4$ to $C_7$ isoolefins will, of course, to a large extent determine the composition of the ether product.

Of the above feedstocks, FCC, RCC and TCC are preferred because these hydrocarbon cuts can be used as such, possibly after the removal of heavier cuts ($C_{8+}$). The use of Pyrolysis Gasoline requires that the light cut and the $C_{6+}$ cut be removed before it can be fed into the process. Up to some 10% of the $C_{6+}$ cut can be included in the resulting hydrocarbon mixture, called a Pyrolysis $C_5$ Gasoline, so as to ensure that substantially all of the reactive $C_5$'s of the Pyrolysis Gasoline are present in the olefinic feedstock. This feedstock will also contain reactive aliphatic $C_{6+}$ hydrocarbons. Pyrolysis Gasoline is particularly rich in isoprene (up to 10 wt-%) and other diolefins, which can be converted to mono-unsaturated hydrocarbons by selective hydrogenation. This will greatly improve the value of this cut as a feedstock for etherification, in particular in combination with any of the above mentioned cracking gasoline cuts.

The process according to the present invention comprises an etherification process wherein a feedstock containing hydrocarbons, in particular $C_{3-7}$ hydrocarbons, is fed into a catalytic distillation reactor system. An alcohol feedstock and a side stream from distillation column are mixed with hydrocarbon feedstock. The $C_{4-7}$ isoolefines of the mixed stream are reacted with an alkanol in the presence of a cation exchange resin to form tertiary alkyl ethers.

When MTBE or ETBE is prepared, a hydrocarbon feed containing in particular reactive $C_4$ hydrocarbons is used. The etherification of isobutene primarily gives rise to the desired alkyl ether. The unreacted $C_4$ and/or $C_5$ portion of the hydrocarbon feed is separated from the either product and conducted to further processing, for example by alkylation. Alkylation is not, however, possible if the $C_4$ and $C_5$ fraction contains oxygenates, such as the unreacted alkanol, i.e. methanol or ethanol, of the etherification reaction.

Accordingly to the present invention, the above aim is reached by the provision of two columns, the bottoms of the first being fed into second column and the ether is recovered as a bottom product of the second column. The first column is operated such that there is no alkanol present in the bottoms product. This is because said alkanol, which is light component, would exit the second column with the overhead product and accompanying unreacted $C_4$'s. In that way, the overhead product would become contaminated and it could not be used for alkylation without further purification.

In the process described in WO 93/19032 for producing TAME, a product which comprises alkyl ethers and substantially all of the unreacted hydrocarbons is recovered from the bottom of the distillation column. The overhead product of the column can be forwarded to a MTBE or ETBE unit. By contrast, in the present process, the bottoms product of the first distillation column is forwarded to a second column from which the MTBE or ETBE product is recovered as the bottoms product.

According to the invention, any catalyst typically used in etherification processes can be employed. Preferably conventional cation exchange resins are used. However also different kinds of zeolites are also possible. Thus, the resin may contain sulfonic acid groups and it can be obtained by polymerization or copolymerization of aromatic vinyl compounds followed by sulfonation. Examples of aromatic vinyl compounds suitable for preparing polymers of copolymers are: styrene, vinyl toluene, vinyl naphthalene, vinyl ethylbenzene, methyl styrene, vinyl chlorobenzene and vinyl xylene. The acid cation exchange resin typically contain some 1.3 to 1.9 sulfonic acid groups per aromatic nucleus. Preferred resins are based on copolymers of aromatic monovinyl compounds with aromatic polyvinyl compounds, particularly, divinyl compounds, in which the polyvinyl benzene content is from about 1 to 20 wt-% of the copolymer. The ion exchange resin preferably has a granular size of about 0.15 to 1 mm. In addition to the above resins perfluorosulfonic acid resins, which are copolymers of sulfonyl fluorovinyl ethyl and fluorocarbon, can be used.

The alkyl ethers are removed from the distillation reactor system with the bottom product and, if desired, subjected to further processing, for instance by distillation to produce a gasoline component. As mentioned above, substantially all of the unreacted and inert $C_4$–$C_7$ hydrocarbons are also removed with the bottoms product of the distillation.

According to the present invention the distillation column of the reactive distillation unit is operated in such a way that the alkanol is heavier than the hydrocarbons at the top of the distillation column. Therefore, the alkanol not bound to the hydrocarbons in the form of an azeotrope will tend to flow downwards within the column. At the same time the vapor-liquid-equilibrium between $C_4$ and heavier hydrocarbons and the alkanol at the bottom of the column is maintained at such a value that the alkanol is lighter than the hydrocarbons. This causes the alkanol to flow upwards from the bottom of the column. Thus, the alkanol will circulate within the distillation system between the top and the bottom of the column. By fitting a reaction bed in the distillation column or by conducting a side stream from the column through a reaction bed in a side reactor, an alkanol consuming reaction can be created which will remove the alkanol from the system.

The alkanols, in particular methanol and ethanol, form azeotropes with the hydrocarbons of the feedstock. The heavier the hydrocarbons, the greater the alkanol concentration of the hydrocarbon-alkanol-azeotrope. According to the present invention, in order to minimize the amount of unreacted alkanol removed from the distillation process, substantially only the $C_3$-hydrocarbon-alkanol azeotropes are taken as an overhead product. These azeotropes are the lightest hydrocarbon-alkanol azeotropes and have the smallest alkanol concentrations.

Thus, according to the present invention, the amount of unreacted alkanol can be controlled by adjusting the amount of $C_3$ hydrocarbons in the feed. The less there are $C_3$ hydrocarbons in the feed, the less distillate can be removed and the less alkanol is removed from the process. By increasing the amount of $C_3$ hydrocarbons in the feed the distillate flow rate can be increased without any change of the relative amount of free unreacted alkanol in the overhead product. Therefore, if desired, $C_3$ hydrocarbons can deliberately be added to the process so that the intended effect is achieved. According to the present invention, the amount of $C_3$ hydrocarbons in the feed should be about 0.01 to 15 wt-% of the hydrocarbon feed, preferably about 0.5 to 4%.

When operating the process according to the invention, the alkanol concentration of the bottoms product of the column can easily be reduced to as small a value as desired. In the case of methanol, it is possible to reduce its concentration in the bottoms product to below 100 ppm. The amount of alkanol in the distillate will correspond to the amount bound by the azeotrope, only. The composition of the azeotrope and, thus, the amount of removed alkanol depends on the hydrocarbon composition of the overhead product and the operating pressure of the distillation.

According to a preferred embodiment of the present invention, the reactive distillation system comprises a distillation column which is in fluid contact with at least one reactor containing a catalytic reaction bed.

Preferably the location of the drawoff (side stream) from the column to the reactors) is selected in such a way that the vapour-liquid equilibrium ratio (the K-value) of the alkanol is smaller than 1 on the (theoretical) trays above it. The reaction product containing the alkanol is directed from the reactors) to the column and it is fed to a tray having an alkanol K-value greater than 1. As a result the alkanol gets more enriched in the vapor phase than do the hydrocarbons. The side stream makes up 40 to 90%, typically about from 60 to about 70% of the total liquid flow within the column. The use of an external reactor is preferred, e.g., for the reason that the conditions prevailing in the distillation column can be influenced by changing the drawoff location of the side stream and by feeding more alkanol to the reaction bed. The invention can also be applied to a conventional catalytic distillation reactor. It is operated in the same way as a side reactor process. The only difference is that the alkanol consuming reaction takes place within the column.

The invention is preferably carried out in connection with the MTBE or mixed ether processes, when the alcohol used is methanol.

Considerable benefits are achieved by means of the invention. Thus, due to the disclosed arrangement all of the unreacted alkanol, which comes out from the distillation column, is bound to an azeotrope. Since the amount of the removed alkanol is small, no separation unit is longer needed. This considerably diminishes the investment cost of the apparatus.

In the following the invention will be described in more detail with reference to FIGS. 1 and 2. FIG. 1 depicts a simplified scheme of an ether process described in working example 2 which can be used to prepare a product containing only one ether compound or a mixture of ethers.

In the test arrangement according to the example, the hydrocarbon feedstock, the methanol and the side stream from distillation are mixed together and the mixture is through reactors 1, 2 and 3, which are filled with ion exchange resin beds. The hydrocarbon feedstock contains hydrocarbons in $C_3$–$C_7$ range. The reactors can be fixed or fluidized bed or tubular reactors. The reactors may be arranged in series, as shown in the drawing, or in parallel. If there are more than two reactors they may also be arranged in series/parallel. Because of the reaction there is a temperature rise in the prereactors in the range from about 5 to about 15° C. depending on the efficiency of the reactor insulation.

From the reactors the mixture is conducted to distillation column 4. The location of the feed point is defined below more specifically. At the bottom of the distillation column 4 there is a steam reboiler 9. The distillation column can be a packed column or one provided with valve, sieve or bubble-cap trays. The overhead of the column is removed via a condenser 10 to a reflux drum 11, from which the overhead is removed by means of a pump 12. A part of the overhead is forwarded to further processing and a part thereof is returned to the distillation column. MTBE and heavier ethers are removed with the bottoms product. In addition to the ethers, the bottoms product also contains unreacted $C_{4+}$ hydrocarbons. The reflux ratio of the distillation process is adjusted so that the distillate amount removed from the process at least substantially corresponds to the amount of $C_3$ hydrocarbons of the feed.

The reflux ratio of the column is preferably from about 1 to 500. Even greater ratios can be used in pilot plant equipment. According to the invention, the reflux ratio is adjusted so that the distillate amount removed from the process at least substantially corresponds to the amount of $C_3$ hydrocarbons of the feed.

From the distillation column 4 a side stream is taken and mixed with fresh hydrocarbon and alkanol feeds as described above.

Figure 2:
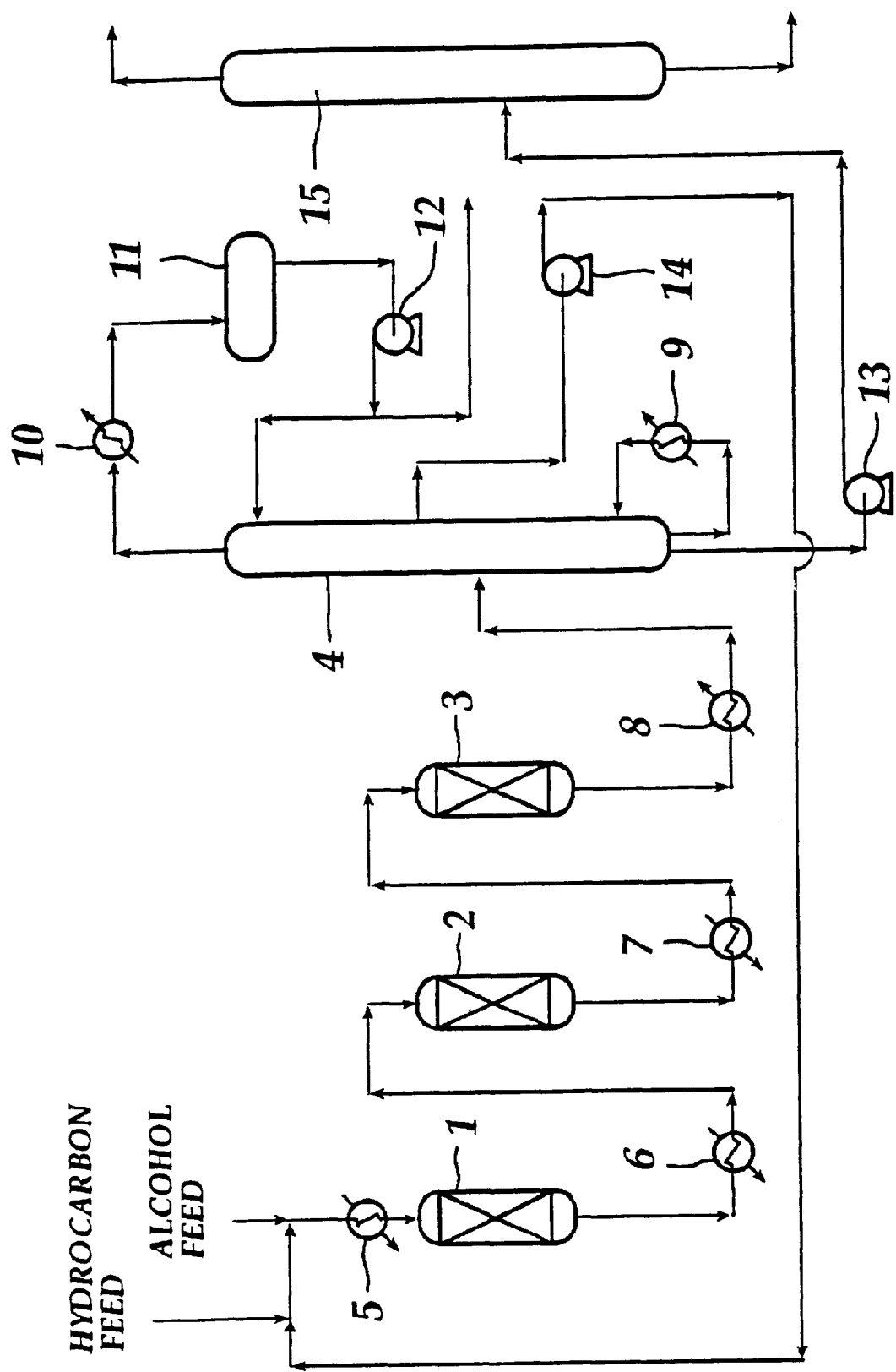
FIG. 2 shows a simplified process scheme for the etherification process in combination with a column for ether separation.

FIG. 2 shows a further improvement of the above-described embodiment. The main difference between the two processes is that, in order to provide a $C_4$ fraction or a $C_4$–$C_5$ fraction suitable for further processing by alkylation, there is a second distillation column 15, which is used for separating the $C_4$ and/or $C_5$ hydrocarbons from the ethers. Normally, only so much $C_4$ and/or $C_5$ hydrocarbons are taken in the overhead product that no MTBE/ETBE will go into said product.

It should thus be noted that when MTBE or ETBE is prepared, an ether-containing stream will be recovered from the first column as the bottoms product and fed into the ether separation column 15, from which the pure ether is recovered from the bottom since no ether is present in the overhead. The overhead product of the distillation column comprises $C_4$ hydrocarbon and contains no MTBE or ETBE.

In the art, by alkylation is meant a process for producing high-octane fuel components (alkylates) from liquid gas cuts, butenes, isobutane. 2,2-dimethylhexane can be determined as an example of an alkylate.

The following working examples will clarify the invention:

EXAMPLE 1

Preparation of ETBE by Using a Catalytic Distillation Reactor System with Two Reactors The apparatus configuration depicted in FIG. 1 is employed with the exception that only two reactors (reactors 1 and 2) are used. The main column contains 60 theoretical trays, the reflux ratio is 80 and the operational pressure 1400 kPa. The temperature at the top of the column is 38.4° C. and at the bottom 100.8° C. The reactor 1 is operated adiabatically and its temperatures from inlet to outlet are 56.0 and 70.0° C., respectively. The reactor 2 is also operated adiabatically and its temperatures from inlet to outlet are 39.9 and 42.0° C., respectively.

The hydrocarbon feedstock (30.0 kg/h) comprises a $C_4$ stream from a FCC unit having the following composition:

| | |
|---|---|
| C$_3$ | 3.50 wt % |
| Isobutene | 17.00 wt % |
| C$_4$ remain. | 76.55 wt % |
| 2-Methyl-2-Butene | 0.09 wt % |
| C$_5$ remain. | 2.86 wt % |
| Total | 100.00 wt % |

The feedstock contains no ethanol or ETBE. All of the ethanol used for the etherification reaction is fed into the reactors. The ethanol feed amounts to 4.06 kg/h.

Table 1 indicates the products of the ETBE preparation process.

TABLE 1

Products of the ETBE process

| | Distillation Column | |
|---|---|---|
| | Distillate wt % | Bottoms product wt % |
| C$_3$ | 84.44 | 0.01 |
| Isobutene | 0.15 | 0.76 |
| C$_4$ remain. | 15.40 | 69.38 |
| 2-Methyl-2-Butene | 0.00 | 0.28 |
| C$_5$ | 0.00 | 2.37 |
| EtOH | 0.01 | 0.24 |
| ETBE | 0.00 | 26.88 |
| TAEE | 0.00 | 0.08 |
| Total | 100.00 | 100.00 |
| Amount, kg/h | 1.24 | 32.83 |

EXAMPLE 2

Preparation of Mixed Ethers by Using a Catalytic Distillation Reactor System with Three Reactors The apparatus configuration depicted in FIG. 1 is used. The main column contains 60 theoretical trays, the reflux ratio is 100 and the operational pressure 1400 kPa. The temperature at the top of the column is 48° C. and at the bottom 141° C. The reactors is operated adiabatically and their temperatures are shown below:

| | Inlet, ° C. | Outlet, ° C. |
|---|---|---|
| Reactor 1 | 43 | 56 |
| Reactor 2 | 56 | 58 |
| Reactor 3 | 39 | 40 |

The hydrocarbon feedstock (30.0 kg/h) comprises a C$_4$ stream from a FCC unit and FCC light gasoline, the mixture having the following composition:

| | |
|---|---|
| C$_3$ | 1.25 wt % |
| Isobutene | 5.33 wt % |
| C$_4$ remain. | 22.30 wt %p |
| 2-Methyl-1-Butene | 1.10 wt % |
| 2-Methyl-2-Butene | 7.90 wt % |
| C$_5$ remain. | 24.53 wt %p |
| C$_6$ reactive | 9.75 wt % |
| C$_6$ remain. | 27.84 wt % |
| Total | 100.00 wt % |

The feedstock contains no methanol or ethers. All of the methanol used for the etherification reactions is fed into the reactors. The methanol feed amounts to 2.43 kg/h.

Table 2 indicates the products of the mixed ether preparation process.

TABLE 2

Products of the mixed ether process

| | Distillation Column | |
|---|---|---|
| | Distillate wt % | Bottoms product wt % |
| C$_3$ | 74.26 | 0.12 |
| Isobutene | 0.04 | 0.02 |
| C$_4$ remain. | 23.62 | 20.56 |
| 2-Methyl-1-Butene | 0.00 | 0.12 |
| 2-Methyl-2-Butene | 0.00 | 1.97 |
| C$_5$ remain. | 0.00 | 23.03 |
| C$_6$ reactive | 0.00 | 4.37 |
| C$_6$ remain. | 0.00 | 26.12 |
| MeOH | 2.08 | 0.01 |
| MTBE | 0.00 | 7.83 |
| TAME | 0.00 | 9.24 |
| THME | 0.00 | 6.60 |
| Total | 100.00 | 100.00 |
| Amount, kg/h | 0.45 | 31.98 |

EXAMPLE 3

Preparation of MTBE

The reactor configuration according to FIG. 2 was used for the preparation of MTBE. The condition of the process indicated in the following table, which also gives the composition of the following streams:

the feed streams of the first column (designated "feed" and "MeOH", respectively)

the overhead of the first column (designated "C$_3$")

the side drawoff (designated "SIDE")

the bottoms product of the first column (designated "BOT")

the overhead of the second column (designated "C$_4$")

the bottoms product of the second column (designated "MTBE").

TABLE 3

| w-% | feed | MeOH | $C_3$ | SIDE | BOT | $C_4$ | MTBE |
|---|---|---|---|---|---|---|---|
| Water | 0.00 | 0.05 | 0.56 | 0.00 | 0.00 | 0.00 | 0.00 |
| DME | 0.00 | 0.00 | 0.04 | 0.00 | 0.00 | 0.00 | 0.00 |
| T-2-Butene | 8.42 | 0.00 | 0.22 | 4.99 | 7.55 | 11.01 | 0.00 |
| IC5 | 0.32 | 0.00 | 0.00 | 0.01 | 0.29 | 0.42 | 0.01 |
| NC5 | 0.13 | 0.00 | 0.00 | 0.00 | 0.11 | 0.06 | 0.24 |
| MeOH | 0.0000 | 99.9502 | 3.3678 | 0.6690 | 0.0012 | 0.0017 | 0.0000 |
| NC6 | 0.13 | 0.00 | 0.00 | 0.00 | 0.11 | 0.00 | 0.36 |
| Isobutylene | 22.69 | 0.00 | 0.36 | 0.80 | 0.47 | 0.69 | 0.00 |
| MTBE | 0.00 | 0.00 | 0.00 | 0.00 | 31.10 | 0.00 | 99.12 |
| Propane | 0.23 | 0.00 | 19.62 | 0.28 | 0.00 | 0.01 | 0.00 |
| Propylene | 0.23 | 0.00 | 19.85 | 0.24 | 0.00 | 0.00 | 0.00 |
| Isobutane | 20.33 | 0.00 | 43.40 | 43.45 | 17.78 | 25.91 | 0.00 |
| 1Butene | 20.34 | 0.00 | 10.42 | 28.23 | 18.14 | 26.43 | 0.00 |
| 13butadiene | 0.60 | 0.00 | 0.25 | 0.76 | 0.53 | 0.77 | 0.00 |
| $NC_4$ | 12.99 | 0.00 | 1.03 | 10.33 | 11.65 | 16.97 | 0.00 |
| c-2-Butene | 13.59 | 0.00 | 0.88 | 10.23 | 12.18 | 17.75 | 0.00 |
| DIB | 0.00 | 0.00 | 0.00 | 0.00 | 0.08 | 0.00 | 0.27 |
| Mass flow, kg/H | 30.00 | 3.79 | 0.35 | 46.75 | 33.44 | 22.95 | 10.49 |
| Temperature, °C. | 45 | 35 | 58.5 | 90.2 | 104.9 | 52.4 | 122.3 |
| Pressure, kPa | 2400 | 2400 | 1500 | 1535 | 1560 | 600 | 648 |

As will appear from the table, the overhead of the first column contains essentially all $C_3$ hydrocarbons of the feed;

the unreacted $C_4$'s are in the bottoms of the first column and methanol is removed with the overhead product of the first column, whereas the bottoms is free from methanol.

What is claimed:

1. Process for preparing an MTBE or ETBE comprising the steps of:

feeding a feedstock mainly containing $C_{3-5}$ hydrocarbons, to a catalytic distillation reactor system, reacting the $C_{4-5}$ isoolefines of the feedstock with methanol or ethanol in the presence of a catalyst to form tertiary alkyl ethers.

removing the alkyl ethers from the distillation reactor and the majority of the unreacted hydrocarbons with the bottoms product of the distillation, withdrawing an overhead product, which mainly contains an azeotrope of $C_3$ hydrocarbons and about as much $C_3$ as in the feedstock, whereby a part of the unreacted alkanol is removed in the form of said azeotrope, conducting the bottoms product of the catalytic distillation reactor system, wherein said bottoms product has an alkanol concentration of less than 100 ppm, to a distillation column, and recovering MTBE or ETBE in the form of the bottoms product of the distillation column and subjecting the overhead product to alkylation.

2. The process according to claim 1, wherein said overhead product comprises $C_4$ hydrocarbons and contains no MTBE or ETBE and is recovered from the distillation column.

3. The process according to claim 1, wherein the amount of distillate withdrawn from the distillation contains about as much $C_3$ hydrocarbons as are present in the feed.

4. The process according to claim 1, wherein the alkanol is heavier than the hydrocarbons at the top of the distillation column and the alkanol is lighter than the $C_4$ and heavier hydrocarbons at the bottom of the distillation column.

5. The process according to claim 1, wherein the amount of unreacted alkanol removed from the process is controlled by adjusting the concentration of $C_3$ hydrocarbons in the feed.

6. The process according to claim 1, wherein the catalytic etherification reaction is carried out in a reactor or reactor system external to the distillation column by withdrawing a sidestream from the column, combining it with a fresh feed of hydrocarbons and recirculating it to the external reactor or reactor system.

7. The process according to claim 1, wherein the catalytic etherification reaction is carried out in a reactor or reactor system external to the distillation column by circulating a sidestream taken from the column through the reactor and returning it to a tray below the one from which it was taken, further comprising adjusting the K-value of the alkanol to less than 1 on the trays above the drawoff tray.

8. The process according to claim 6 or 7, wherein the K-value of the alkanol is adjusted to less than 1 on the trays above the drawoff tray.

9. The process according to claim 6 or 7, wherein the reactor effluent is returned to the column at a point where the K-value of the alkanol is greater than 1.

10. The process according to claim 1, wherein the $C_3$ hydrocarbon concentration of the feed is intentionally kept so small that the mixture formed by the distillate and the bottoms product can be used as such as a component of motor fuel.

11. The process according to claim 1, wherein the catalyst comprises an acid cation exchange resin.

12. The process to claim 1, wherein a mixture is prepared from heavier ethers and at least one member selected from the group comprising MTBE and ETBE.

13. The process according to claim 1, wherein the catalytic etherification reaction is carried out in a reactor or reactor system external to the distillation column by withdrawing a sidestream from the column, combining it with a fresh feed of hydrocarbons and alkanol and recirculating it to the external reactor or reactor system.

* * * * *